(12) United States Patent
Nixon et al.

(10) Patent No.: US 11,884,468 B2
(45) Date of Patent: Jan. 30, 2024

(54) PACKAGING CONTAINER AND METHOD OF MAKING AND USING THE SAME

(71) Applicant: SAINT-GOBAIN PERFORMANCE PLASTICS CORPORATION, Solon, OH (US)

(72) Inventors: Thomas R. Nixon, Au Gres, MI (US); Clemens E. Zoellner, Bay City, MI (US); Jason Osentoski, Gladwin, MI (US); Joshua Martell, Midland, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 0 days.

(21) Appl. No.: 17/646,246

(22) Filed: Dec. 28, 2021

(65) Prior Publication Data

US 2022/0204232 A1 Jun. 30, 2022

Related U.S. Application Data

(60) Provisional application No. 63/132,988, filed on Dec. 31, 2020.

(51) Int. Cl.
*B65D 71/50* (2006.01)
*A61B 50/30* (2016.01)
(Continued)

(52) U.S. Cl.
CPC .......... *B65D 71/50* (2013.01); *A61B 50/3001* (2016.02); *B65D 81/18* (2013.01); *B65D 85/24* (2013.01)

(58) Field of Classification Search
CPC .... A61B 50/3001; A61B 50/30; B65D 71/50; B65D 81/18; B65D 85/24; B65D 75/32; B65D 75/52; B65D 77/00
(Continued)

(56) References Cited

U.S. PATENT DOCUMENTS

| 3,074,540 A | * | 1/1963 | Beich | ..................... B65D 75/36 206/469 |
| 3,574,306 A | * | 4/1971 | Alden | ................... A61M 25/02 206/365 |

(Continued)

FOREIGN PATENT DOCUMENTS

| DE | 8911659 U1 | 11/1989 |
| DE | 102006004082 A1 | 8/2007 |

(Continued)

OTHER PUBLICATIONS

International Search Report and Written Opinion for PCT/US2021/073141, dated May 2, 2022, 10 pages.

*Primary Examiner* — Bryon P Gehman
(74) *Attorney, Agent, or Firm* — Abel Schillinger, LLP; Chi Suk Kim (57) ABSTRACT

The present application is directed to a packaging container including a body including; a first portion including a coupling feature; a second portion including a coupling feature and complementary to the first portion; and a hinge portion coupling the first portion to the second portion adapted to move the packaging container from an open position to a closed position around a product, where the first portion and the second portion combine to form a void port in the closed position.

20 Claims, 4 Drawing Sheets

(51) Int. Cl.
*B65D 85/24* (2006.01)
*B65D 81/18* (2006.01)

(58) Field of Classification Search
USPC .............................. 206/363–370, 380, 526
See application file for complete search history.

(56) References Cited

U.S. PATENT DOCUMENTS

| | | | |
|---|---|---|---|
| 3,613,879 A * | 10/1971 | Kemble | B65D 75/326 |
| | | | 206/467 |
| 4,736,844 A | 4/1988 | Scott et al. | |
| 4,886,165 A | 12/1989 | Annett | |
| 5,133,454 A * | 7/1992 | Hammer | A61M 5/3205 |
| | | | 206/364 |
| 5,193,679 A * | 3/1993 | White | A61F 2/4637 |
| | | | 206/363 |
| 5,842,567 A * | 12/1998 | Rowe | A61B 50/3001 |
| | | | 206/464 |
| 5,853,087 A | 12/1998 | Sos et al. | |
| 6,358,241 B1 * | 3/2002 | Shapeton | A61B 18/14 |
| | | | 206/365 |
| 6,439,276 B1 * | 8/2002 | Wood | A61M 5/3205 |
| | | | 141/97 |
| 6,595,361 B2 | 7/2003 | Sugama | |
| 6,651,813 B2 | 11/2003 | Vallans et al. | |
| 9,333,289 B1 | 5/2016 | Hirschmann et al. | |
| 9,517,298 B2 | 12/2016 | Banik | |
| 9,566,118 B2 | 2/2017 | Dasbach et al. | |
| 10,010,680 B2 | 7/2018 | Limaye et al. | |
| 10,710,759 B2 | 7/2020 | Lu et al. | |
| 10,773,014 B2 | 9/2020 | Maasarani | |
| 2007/0295620 A1 * | 12/2007 | Collet | A61F 2/0095 |
| | | | 206/368 |
| 2008/0035495 A1 | 2/2008 | Discko, Jr. | |
| 2018/0085515 A1 | 3/2018 | Mide et al. | |

FOREIGN PATENT DOCUMENTS

| | | |
|---|---|---|
| EP | 0242035 A1 | 10/1987 |
| EP | 1192914 A1 | 4/2002 |
| EP | 3323445 A1 | 5/2018 |
| EP | 3466466 A2 | 4/2019 |
| EP | 3291856 B1 | 1/2020 |
| JP | 2011005182 A | 1/2011 |
| JP | 6247291 B2 | 12/2017 |
| JP | 2018518262 A | 7/2018 |
| WO | 2022147441 A1 | 7/2022 |

* cited by examiner

PACKAGING CONTAINER AND METHOD OF MAKING AND USING THE SAME

CROSS-REFERENCE TO RELATED APPLICATION(S)

This application claims priority under 35 U.S.C. § 119(e) to U.S. Provisional Application No. 63/132,988, entitled "PACKAGING CONTAINER AND METHOD OF MAKING AND USING THE SAME," by Thomas R. NIXON et al., filed Dec. 31, 2020, which is assigned to the current assignee hereof and incorporated herein by reference in its entirety.

FIELD OF THE DISCLOSURE

The present disclosure relates to a packaging container, and more particularly to, a packaging container for housing a sensitive product such as a medical, biological, or pharmaceutical product.

RELATED ART

Packaging containers are used for packaging many products shipped and sold. In some cases, packaging containers may be used to ship sensitive products that are used in clean room or sterilized conditions, such as medical, biological, or pharmaceutical products. In some cases, these packaging containers may be used to house needles, needle assemblies and other sharps that may be damaged or puncture their packaging containers during shipping, which may limit or destroy the intended use of these products. Therefore, improvements in packaging containers are needed, particularly in enabling packaging containers to protect needles, needle assemblies and other sharps while allowing improved ease of use.

BRIEF DESCRIPTION OF THE DRAWINGS

Embodiments are illustrated by way of example and are not limited in the accompanying figures.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single embodiment is described herein, more than one embodiment may be used in place of a single embodiment. Similarly, where more than one embodiment is described herein, a single embodiment may be substituted for that more than one embodiment.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the packaging container arts.

The following disclosure describes packaging containers adapted to achieve substantial seal engagement to the container to ensure an adequate seal in assembling a packaging container and container. The concepts are better understood in view of the embodiments described below that illustrate and do not limit the scope of the present invention.

Figure 1A:
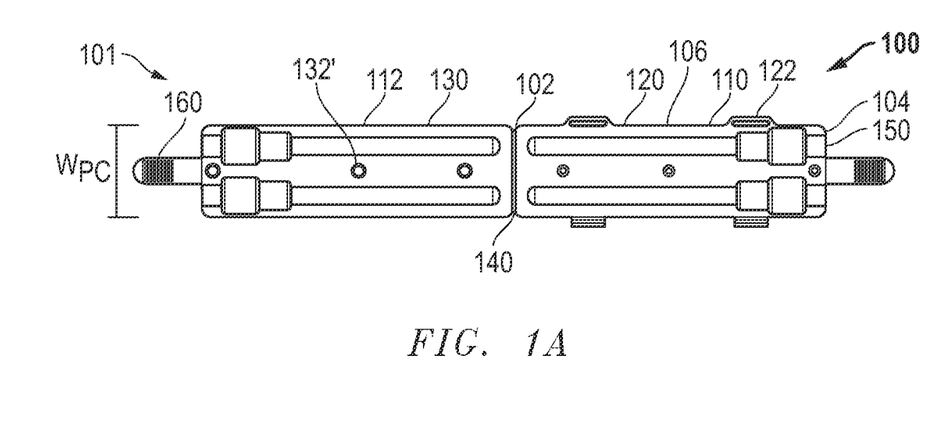
FIG. 1A illustrates a top view of a packaging container in an open position according to a number of embodiments of the present disclosure.
Figure 1B:
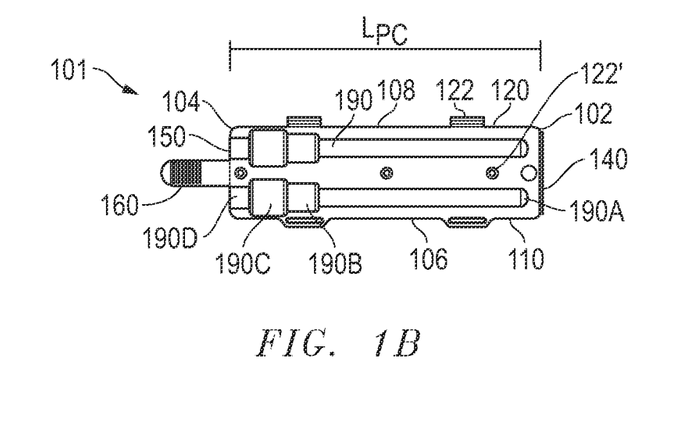
FIG. 1B illustrates a top view of a packaging container in a closed position according to a number of embodiments of the present disclosure.
Figure 1C:
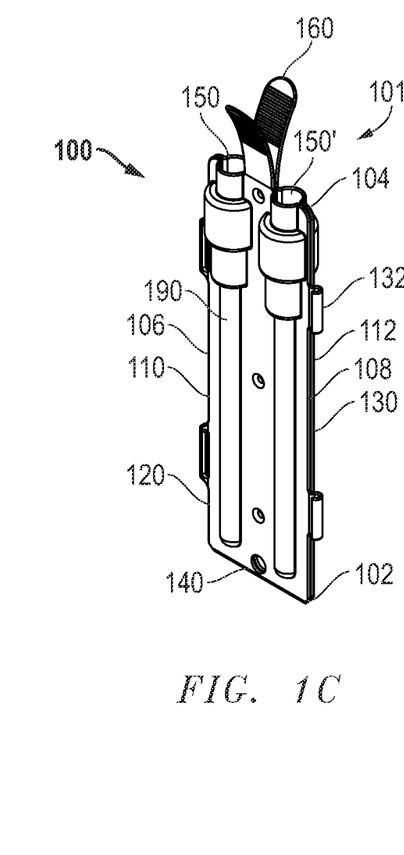
FIG. 1C illustrates a side view of a packaging container in a closed position according to a number of embodiments of the present disclosure.

For purposes of illustration, FIG. 1A illustrates a top view of a packaging container in an open position according to a number of embodiments of the present disclosure. FIG. 1B illustrates a top view of a packaging container in a closed position according to a number of embodiments of the present disclosure. FIG. 1C illustrates a side view of a packaging container in a closed position according to a number of embodiments of the present disclosure.

As best illustrated in FIGS. 1A-1C, the packaging container 100 may include a body 101. The body 101 may include a first end 102, a second end 104, a third end 104, and a fourth end 108. The packaging container 100 may include a first face (or front side) 110 and a second face (or back side) 112 opposite the first face 100. In a number of embodiments, the first face 110 of the packaging container 100 may be generally polygonal cross-section (e.g. rectangular). In a number of variations, the first face 110 of the packaging container 100 may have a polygonal, oval, circular, semi-circular, or substantially circular cross-section. In a number of embodiments, the first face 110 of the packaging container 100 may be generally flat. In a number of embodiments, the second face 112 of the packaging container 100 may be generally polygonal cross-section (e.g. rectangular). In a number of variations, the second face 112 of the packaging container 100 may have a polygonal, oval, circular, semi-circular, or substantially circular cross-section. In a number of embodiments, the second face 112 of the packaging container 100 may be generally flat.

In a number of embodiments, the packaging container 100 may have a width $W_{PC}$. For purposes of embodiments described herein and as shown in FIG. 1, the width $W_{PC}$ of the packaging container 100 is the distance from the third end 104 to the fourth end 108. According to certain embodiment, the width $W_{PC}$ of the packaging container 100 may be at least about 100 mm, such as, at least about 150 mm or at least about 200 mm or at least about 250 mm or at least about 300 mm or even at least about 500 mm. According to still other embodiments, the width $W_{PC}$ of the packaging container 100 may be not greater than about 1500 mm, such as, not greater than about 1200 mm or even not greater than about 1000 mm. It will be appreciated that the width $W_{PC}$ of the packaging container 100 may be within a range between any of the minimum and maximum values noted above. It will be further appreciated that the width $W_{PC}$ of the packaging container 100 may be any value between any of the minimum and maximum values noted above.

In a number of embodiments, the packaging container 100 can have a length $L_{PC}$. For purposes of embodiments described herein and as shown in FIG. 1, the length $L_{PC}$ of the packaging container 100 is the distance from the first end 102 to the second end 104. According to certain embodiment, the length $L_{PC}$ of the packaging container 100 may be at least about 100 mm, such as, at least about 150 mm or at least about 200 mm or at least about 250 mm or at least about 300 mm, or even at least about 500 mm. According to still other embodiments, the length $L_{PC}$ of the packaging container 100 may be not greater than about 1500 mm, such as, not greater than about 1200 mm or even not greater than about 1000 mm. It will be appreciated that the length $L_{PC}$ of the packaging container 100 may be within a range between any of the minimum and maximum values noted above. It will be further appreciated that the length $L_{PC}$ of the packaging container 100 may be any value between any of the minimum and maximum values noted above.

In a number of embodiments, the body 101 may form a first portion 120 and a second portion 130. The first portion 120 may include the first face 110. The second portion 130 may include the second face 112. The second portion 130 may be complementary to the first portion 120. The body 101 may further include a hinge portion 140 coupling the first portion 120 to the second portion 130. The hinge portion 140 may be located at the first end 102 of the packaging container 100. The hinge portion 140 may allow for and/or be adapted to move the packaging container 100 from an "open position" from a "closed position" to form a packaging void 190 for housing a product (not shown) and forming a packaging assembly. The hinge portion 140 may be flexible and allow the first portion 120 to fold over onto the second portion 120 or vice versa. The packaging void 190 may be shaped to better house the product. The product may include a medical, biological, or pharmaceutical device, such as a needle, needle assembly, syringe, lancet, auto injector, infusion set, connection needle, or may be another sharp. The product may include medical tubing. In specific embodiments, the packaging system may contain a product type for biopharma/life sciences that are designed for a single use. In a number of embodiments, the packaging void 190 may include a first portion 190A, a second portion, 190B, a third portion 190C, and a fourth portion 190D. The first portion 190A may be adapted to house a component of the product, such as, but not limited to, a needle shaft. The second portion 190B may be adapted to house a component of the product, such as, but not limited to, a needle hub. The third portion 190C may be adapted to house a component of the product, such as, but not limited to, a needle adapter. The fourth portion 190D may be adapted to house a component of the product, such as, but not limited to, a needle connection to another component such as a tube as explained in further detail below.

In a number of embodiments, the packaging container 100 may have a thickness $T_{PC}$. For purposes of embodiments described herein and as shown in FIG. 1, the thickness $T_{PC}$ of the packaging container 100 is the distance between the first face 110 and the second face 112 may be at least about 0.001 mm, such as, at least about 0.005, 0.1 mm or at least about 0.2 mm or at least about 0.3 mm or at least about 0.4 mm or even at least about 0.5 mm. According to still other embodiments, the thickness $T_{PC}$ of the packaging container 100 may be not greater than about 500 mm, such as, not greater than about 250 mm or even not greater than about 100 mm. It will be appreciated that the thickness $T_{PC}$ of the packaging container 100 may be within a range between any of the minimum and maximum values noted above. It will be further appreciated that the thickness $T_{PC}$ of the packaging container 100 may be any value between any of the minimum and maximum values noted above. In a number of embodiments, the thickness $T_{PC}$ of the packaging container 100 may be at least 2 mil and no greater than 15 mil.

The first portion 110 may include a coupling feature 122. In a number of embodiments, the first portion 110 may include a plurality of coupling features 122. The coupling feature 122 of the first portion 110 may include a fastener including at least one of screw threads or threadings, screws, bolts, clamps, clasps, clips, latches, pins, rivets, ties, nails, battens, buckle, flange, frog, grommet, hook-and-eye, peg, screw anchor, snap fastener, stitch, threaded fastener, tie, toggle bolt, wedge anchor, pin, groove and stop, nut and bolt, nut and screw, latch, handle, locking nut, tie rivet, male and female attachments, interlock attachments, tongue- and groove attachments, or may be another type. As shown in FIGS. 1A-1C, the coupling feature 122 may be a male attachment that interlocks with a complementary female attachment of the second portion 130. Further, the coupling feature 122 may include at least one punch 122' to further provide structure and integrity to the packaging container 100. The punches 122' may allow a user to press areas of the first portion 120 and the second portion 130 together while still maintaining the packaging void 190.

The second portion 130 may include a coupling feature 132. In a number of embodiments, the second portion 130 may include a plurality of coupling features 132. The coupling feature 132 of the second portion 130 may include a fastener including at least one of screw threads or threadings, screws, bolts, clamps, clasps, clips, latches, pins, rivets, ties, nails, battens, buckle, flange, frog, grommet, hook-and-eye, peg, screw anchor, snap fastener, stitch, threaded fastener, tie, toggle bolt, wedge anchor, pin, groove and stop, nut and bolt, nut and screw, latch, handle, locking nut, tie rivet, male and female attachments, interlock attachments, tongue- and groove attachments, or may be another type. As shown in FIGS. 1A-1C, the coupling feature 132 may be a female attachment that interlocks with a complementary male attachment of the first portion 110. Further, the coupling feature 132 may include at least one punch 132' to further provide structure and integrity to the packaging container 100. The punches 132' may allow a user to press areas of the first portion 120 and the second portion 130 together while still maintaining the packaging void 190.

In particular embodiments, packaging container 200 may include a tearable, peelable, or snappable tab 160 to form an open position upon application of force. The tearable, peelable, or snappable tab 160 may be located at the second end 104 of the packaging container 100. The packaging container 200 may include a plurality of tearable, peelable, or snappable tabs 160, one on the first portion 120 and one on the second portion 130. The tearable, peelable, or snappable tab 160 may include a peelable or snappable film adapted to at least partially seal the first portion and the second portion in the closed position. The tearable, peelable, or snappable tab 160 may be unsealed by a user by peeling or unsnapping the peelable or snappable film by an application of force. The application of force may be no greater than about 10 lbf, no greater than about 5 lbf, no greater than about 2.5 lbf, no greater than about 2 lbf, or no greater than about 1 lbf.

In a number of embodiments, the packaging container 200 may include a void port 150. The void port 150 may house the product such that the product is partially inside the packaging container (i.e. within the void portion 190) while also being partially outside of the packaging container 100 in the closed position. This may facilitate easy use of the product while simultaneously housing the product and allowing for easy removal or insertion of the product from the packaging container 200 in the closed position. In some embodiments, the void port 150 may house a connecting tube connecting to a needle assembly through a needle connection as discussed in more detail below.

Figure 2A:
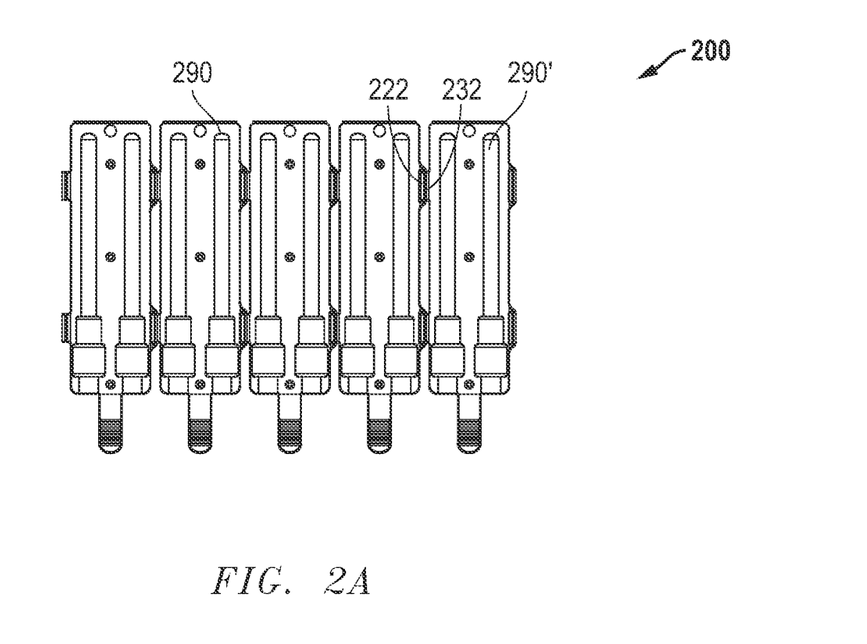
FIG. 2A illustrates a top view of a packaging container in a closed position according to a number of embodiments of the present disclosure.
Figure 2B:
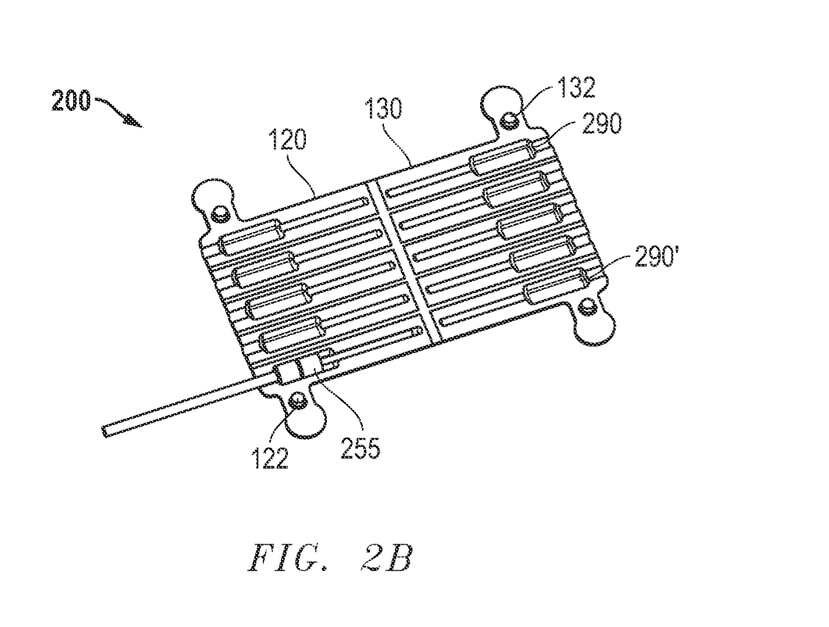
FIG. 2B illustrates a top view of a packaging container in an open position according to a number of embodiments of the present disclosure.

For purposes of illustration, FIG. 2A illustrates a top view of a packaging container in a closed position according to a number of embodiments of the present disclosure. FIG. 2B illustrates a top view of a packaging container in an open position according to a number of embodiments of the present disclosure. As shown in FIGS. 2A and 2B, the packaging container 200 may include a plurality of packaging voids 290, 290' adapted for housing a plurality of products 255. The plurality of packaging voids 290, 290' may be separable from each other (for example using snap coupling features 222, 232 shown in FIG. 2B). As shown in FIG. 2B, the coupling features 222, 232 may include a flexible male/female snap attachment.

Figure 3A:
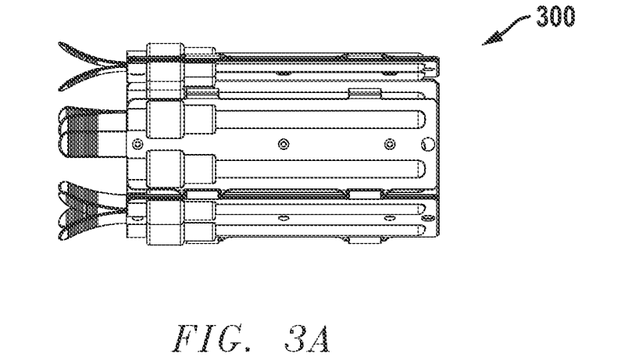
FIG. 3A illustrates a side view of a packaging container according to a number of embodiments of the present disclosure.
Figure 3B:
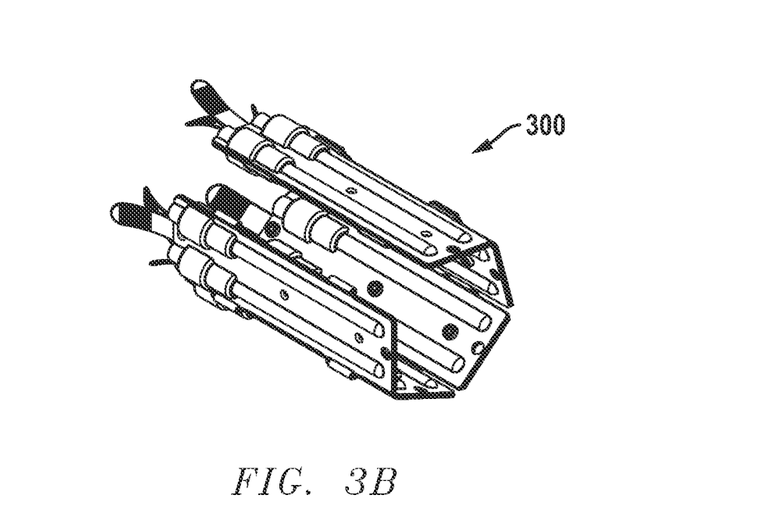
FIG. 3B illustrates a top view of a packaging container according to a number of embodiments of the present disclosure.
Figure 3C:
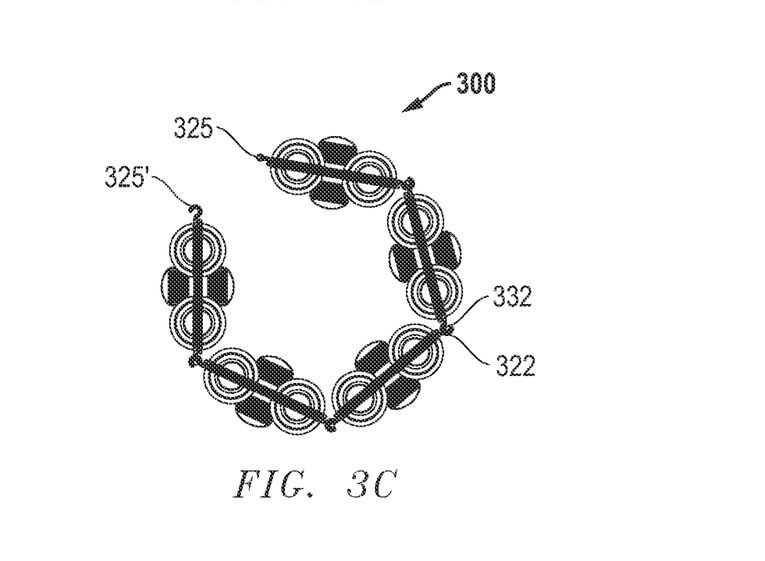
FIG. 3C illustrates a perspective view of a packaging container according to a number of embodiments of the present disclosure.

For purposes of illustration, FIG. 3A illustrates a side view of a packaging container according to a number of embodiments of the present disclosure. FIG. 3B illustrates a top view of a packaging container according to a number of embodiments of the present disclosure. FIG. 3C illustrates a perspective view of a packaging container according to a number of embodiments of the present disclosure. As shown in FIGS. 3A-3B, the packaging container 300 may be capable of folding, rolling, or condensing so as to form a rollable or foldable position. In a number of embodiments, the packaging container 300 may include a locking mechanism 325 adapted to lock the plurality of packaging voids 390 together in a rollable or foldable position. The locking mechanism 325 may include a fastener including at least one of screw threads or threadings, screws, bolts, clamps, clasps, clips, latches, pins, rivets, ties, nails, battens, buckle, flange, frog, grommet, hook-and-eye, peg, screw anchor, snap fastener, stitch, threaded fastener, tie, toggle bolt, wedge anchor, pin, groove and stop, nut and bolt, nut and screw, latch, handle, locking nut, tie rivet, male and female attachments, interlock attachments, tongue- and groove attachments, or may be another type. As shown in FIG. 3C, the locking mechanism 325 may be a hook attachment 325 that interlocks with a ring attachment 325'. As shown in FIG. 3C, the coupling features 322, 332 may include a flexible male/female circular snap attachment which may aid in allowing the packaging container to fold or roll. In a number of embodiments, the packaging container may be capable of forming a stackable position. This may include stacking multiple packaging voids on top of one another.

In particular embodiments, at least one of the components of the packaging container can be formed of a material including a polymer. In a number of embodiments, at least one of the components of the packaging container can be formed of a rigid material including a polymer. In an embodiment, at least one of the components of the packaging container may include a blend or composition of polymers including a thermoplastic elastomeric hydrocarbon block copolymer, a polyether-ester block co-polymer, a thermoplastic polyamide elastomer, a thermoplastic polyurethane elastomer, a thermoplastic polyolefin elastomer, a thermoplastic vulcanizate, an olefin-based co-polymer, an olefin-based ter-polymer, a polyolefin plastomer, or combinations thereof. In an embodiment, at least one of the components of the packaging container may include a styrene based block copolymer such as styrene-butadiene, styrene-isoprene, blends or mixtures thereof, mixtures thereof, and the like. Exemplary styrenic thermoplastic elastomers include triblock styrenic block copolymers (SBC) such as styrene-butadiene-styrene (SBS), styrene-isoprene-styrene (SIS), styrene-ethylene butylene-styrene (SEBS), styrene-ethylene propylene-styrene (SEPS), styrene-ethylene-ethylene-butadiene-styrene (SEEBS), styrene-ethylene-ethylene-propylene-styrene (SEEPS), styrene-isoprene-butadiene-styrene (SIBS), or combinations thereof. Commercial examples include some grades of Kraton™ and Hybrar™ resins.

In an embodiment, at least one of the components of the packaging container may include a polyolefin polymer. A typical polyolefin may include a homopolymer, a copolymer, a terpolymer, an alloy, or any combination thereof formed from a monomer, such as ethylene, propylene, butene, pentene, methyl pentene, hexene, octene, or any combination thereof. In an embodiment, the polyolefin polymer may be copolymers of ethylene with propylene or alpha-olefins or copolymers of polypropylene with ethylene or alpha-olefins made by metallocene or non-metallocene polymerization processes. Commercial polyolefin examples include Affinity™, Engage™, Flexomer™, Versify™, Infuse™, Exact™, Vistamaxx™, Softel™ and Tafmer™, Notio™ produced by Dow, ExxonMobil, Londel-Basell and Mitsui. In an embodiment, the polyolefin polymer may include copolymers of ethylene with polar vinyl monomers such as acetate (EVA), acrylic acid (EAA), methyl acrylate (EMA), methyl methacrylate (EMMA), ethyl acrylate (EEA) and butyl acrylate (EBA). Exemplary suppliers of these ethylene copolymer resins include DuPont, Dow Chemical, Mitusi and Arkema etc. In another embodiment, the polyolefin polymer can be a terpolymer of ethylene, maleic anhydride and acrylates such as Lotader™ made by Arkema and Evalloy™ produced by DuPont. In yet another embodiment, the polyolefin polymer can be an ionomer of ethylene and acrylic acid or methacrylic acid such as Surlyn™ made by DuPont. In an embodiment, the polyolefin is a reactor grade thermoplastic polyolefin polymer, such as P6E2A-005B available from Flint Hills Resources. In an embodiment, at least one of the components of the packaging container may include, but are not limited to, thermoplastic, thermosets, fluropolymers, and combinations thereof. Specific examples of suitable polymer material can be polyvinyldiene fluoride (PVDF). In an embodiment, at least one of the components of the packaging container can be formed of a thermoplastic elastomer, silicone, or combinations thereof.

In an embodiment, at least one of the components of the packaging container may include a fluorinated polymer. In an embodiment, at least one of the components of the packaging container may include at least one of silicone, polydimethylsiloxane (PDMS), functionally modified polydimethylsiloxane, an polytetrafluoroethylene (PTFE), fluorinated ethylene-propylene (FEP), polyvinylidenfluoride (PVDF), polychlorotrifluoroethylene (PCTFE), ethylene chlorotrifluoroethylene (ECTFE), amorphous P.E.T.P., perfluoroalkoxypolymer (PFA), polyacetal (POM), polybutylene terephthalate (PBT), polyimide (PI), polyamidimide (PAI), polyetherimide, polyetheretherketone (PEEK), polyethylene, such as ultrahigh molecular weight polyethylene (UHMWPE), polysulfone, polyamide, polyphenylene oxide, polyphenylene sulfide (PPS), polyurethane, polyester, ethylene-tetrafluoroethylene (ETFE), tetrafluoro-ethylene-perfluoro (methyl vinyl ether) (MFA), polyvinylidene fluoride (PVDF), ethylene-chlorotrifluoroethylene (ECTFE), polyimide (PI), polyamidimide (PAI), polyphenylene sulfide (PPS), polyethersulofone (PES), polyphenylene sulfone (PPSO2), liquid crystal polymers (LCP), polyetherketone (PEK), polyether ether ketones (PEEK), aromatic polyesters (Ekonol), polyetherketone (PEK), liquid crystal polymer (LCP), polyimide (PA), polyethylene (PE), polypropylene (PP), polystyrene, styrene butadiene copolymers, polyesters, polycarbonate, polyacrylonitriles, polyamides, styrenic block copolymers, ethylene vinyl alcohol copolymers, ethylene vinyl acetate copolymers, polyesters grafted with maleic anhydride, poly-vinylidene chloride, aliphatic polyketone, liquid crystalline polymers, ethylene methyl acrylate copolymer, ethylene-norbomene copolymers, polymethylpentene and ethylene acyrilic acid copoloymer, mixtures, copolymers, or any combination thereof.

Further, in an embodiment, at least one of the components of the packaging container can include one or more additives. For example, the one or more additives can include a plasticizer, a catalyst, a silicone modifier, a silicon component, a stabilizer, a curing agent, a lubricant, a colorant, a filler, a blowing agent, another polymer as a minor component, or a combination thereof. In a particular embodiment, the plasticizer can include mineral oil.

In an embodiment, at least one of the components of the packaging container can be formed as a single piece or may be formed as multiple pieces. In an embodiment, at least one of the components of the packaging container can be a molded component. In an embodiment, at least one of the components of the packaging container can be formed through over-molding or other methods known in the art. In an embodiment, the polymer or polymeric blend included in at least one of the components of the packaging container may be processed by any known method to form the polymeric mixture. The polymer or polymeric blend may be melt processed by dry blending or compounding. The dry blend may be in powder, granular, or pellet form. The blend can be made by a continuous twin-screw compounding process or batch related Banbury process. Pellets of these mixtures may then be fed into a single screw extruder to make articles such as flexible tubing products. Mixtures can also be mixed in a single-screw extruder equipped with mixing elements and then extruded directly into articles such as tubing products. In a particular embodiment, the mixture can be melt processed by any method envisioned known in the art such as laminating, casting, molding, extruding, and the like. In an embodiment, the mixture can be injection molded.

In a number of embodiments, the body may be bonded to the peelable or snappable film to form the packaging container. In a number of embodiments, the polymeric composition of the body (including any of the materials listed above) may be bonded to the polymeric composition of the peelable or snappable film (including any of the materials listed above) to form the packaging container. In a number of embodiments, the peelable or snappable film may be peelable or tearable against the body to open the packaging container. In a number of embodiments, the body or peelable or snappable film may form layers of any of the materials listed above. In a number of embodiments, any of the layers on the body or the peelable or snappable film as described above, can each be disposed in a roll and peeled therefrom to join together under pressure, at elevated temperatures (hot or cold pressed or rolled), by an adhesive, or by any combination thereof. Any of the layers of t the body or the peelable or snappable film, as described above, may be laminated together such that they at least partially overlap one another. Any of the layers on the body or the peelable or snappable film as described above, may be applied together using coating technique, such as, for example, physical or vapor deposition, spraying, plating, powder coating, or through other chemical or electrochemical techniques. In a particular embodiment, layers of the body or the peelable or snappable film may be applied by a roll-to-roll coating process, including for example, extrusion coating. The body or the peelable or snappable film may be heated to a molten or semi-molten state and extruded through a slot die onto an interior or exterior surface of the other of the body or the peelable or snappable film to form the packaging container. The packaging container is formed by injection molding, vacuum forming, extrusion, additive manufacturing, or 3-D printing.

In an embodiment, the polymer or polymeric composition of at least one of the components of the packaging container may be formed into a single layer article, a multi-layer article, or can be laminated, coated, or formed on a substrate to form at least one of the components of the packaging container. Multi-layer articles may include layers such as reinforcing layers, adhesive layers, barrier layers, chemically resistant layers, metal layers, any combination thereof, and the like. The polymer or polymeric composition can be formed into any useful shape such as film, sheet, tubing, and the like to form at least one of the components of the packaging container.

In an embodiment, the polymer or polymeric composition of at least one of the components of the packaging container may be formed into a single layer article, a multi-layer article, or can be laminated, coated, or formed on a substrate to form at least one of the components of the packaging container. Multi-layer articles may include layers such as reinforcing layers, adhesive layers, barrier layers, chemically resistant layers, metal layers, any combination thereof, and the like. The polymer or polymeric composition can be formed into any useful shape such as film, sheet, and the like to form at least one of the components of the packaging container.

In an embodiment, the polymer or polymeric blend of the packaging container, the first film composition or the second film composition can advantageously withstand sterilization processes. In an embodiment, the polymer or polymeric blend may be sterilized by any method envisioned. For instance, the polymer or polymeric blend is sterilized after at least one of the components of the packaging container is formed. Exemplary sterilization methods include X-ray radiation, electron ray, E-beam techniques, combinations thereof, and the like. In a particular embodiment, the polymer or polymeric blend is sterilized by vaporized hydrogen peroxide sterilization (VHP). In a particular embodiment, the polymer or polymeric blend is sterilized by gamma irradiation. For instance, the polymer or polymeric blend of at least one of the components of the packaging container may be gamma sterilized at between about 25 kGy to about 50 kGy. In a number of embodiments, the packaging container may be vaporized hydrogen peroxide (VHP) resistant. The packaging container may be VHP resistant at a level of less than 1,000 ppm, such as less than 500 ppm, such as less than 250 ppm, such as less than 100 ppm, such as less than 50 ppm, such as less than 25 ppm, such as less than 10 ppm, such as less than 5 ppm, such as less than 2 ppm, or such as less than 1 ppm.

In an embodiment, at least one of the components of the packaging container may have further desirable physical and mechanical properties. For instance, at least one of the components of the packaging container may appear transparent or at least translucent. For instance, at least one of the components of the packaging container may have a light transmission greater than about 2%, or greater than about 5% in the visible light wavelength range. In particular, the resulting articles have desirable clarity or translucency. In addition, at least one of the components of the packaging container have advantageous physical properties, such as a balance of any one or more of the properties of hardness, flexibility, surface lubricity, tensile strength, elongation, elastic modulus, Shore A hardness, Shore B hardness, gamma resistance, weld strength, and seal integrity to an optimum level.

In a number of embodiments, the packaging container may have a Shore A hardness in the range from 5 to 95, in a range from 15 to 80, in a range from 25 to 70, or in a range from 40 to 60. It will be appreciated that the Shore A hardness of the packaging container may be within a range between any of the minimum and maximum values noted above. It will be further appreciated that the Shore A hardness of the packaging container may be any value between any of the minimum and maximum values noted above.

In a number of embodiments, the packaging container may have a Shore B hardness in the range from 5 to 95, in a range from 15 to 80, in a range from 25 to 70, or in a range from 40 to 60. It will be appreciated that the Shore B hardness of the packaging container may be within a range between any of the minimum and maximum values noted above. It will be further appreciated that the Shore B hardness of the packaging container may be any value between any of the minimum and maximum values noted above.

In a number of embodiments, the peelable or snappable film of the packaging container may have an elastic modulus that is at least 0.5 times, at least 0.55 times, or at least 0.6 times the elastic modulus of the body of the packaging assembly, as defined in ASTM D 412. It will be appreciated that the elastic modulus may be within a range between any of the minimum and maximum values noted above. It will be further appreciated that the elastic modulus may be any value between any of the minimum and maximum values noted above.

In an embodiment, at least one of the components of the packaging container may have desirable heat stability properties. Applications for the polymer or polymeric blend are numerous. In particular, the polymer or polymeric blend is non-toxic, making the material useful for any application where no toxicity is desired. For example, the polymer or polymeric blend may be substantially free of plasticizers or other low-molecular weight extenders that can be leached into the fluids it transfers. "Substantially free" as used herein refers to a polymeric mixture having a total organic content (TOC) (measured in accordance to ISO 15705 and EPA 410.4) of less than about 100 ppm. Further, the polymer or polymeric blend has biocompatiblity and animal derived component-free formulation ingredients. For instance, the polymeric mixture has potential for FDA, USP, EP, ISO, and other regulatory approvals. In an exemplary embodiment, the polymer or polymeric blend may be used in applications such as industrial, medical, health care, biopharmaceutical, pharmaceutical, drinking water, food & beverage, laboratory, dairy, and the like. In an embodiment, the polymeric mixture may be used in applications where low temperature resistance is desired. In an embodiment, the polymer or polymeric blend may also be safely disposed as it generates substantially no toxic gases when incinerated and leaches no plasticizers into the environment if land filled.

Figure 4A:
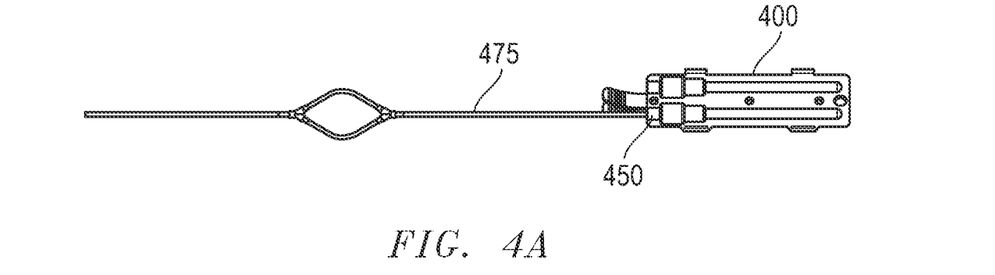
FIG. 4A illustrates a side view of a packaging container attached to a tube according to a number of embodiments of the present disclosure.
Figure 4B:
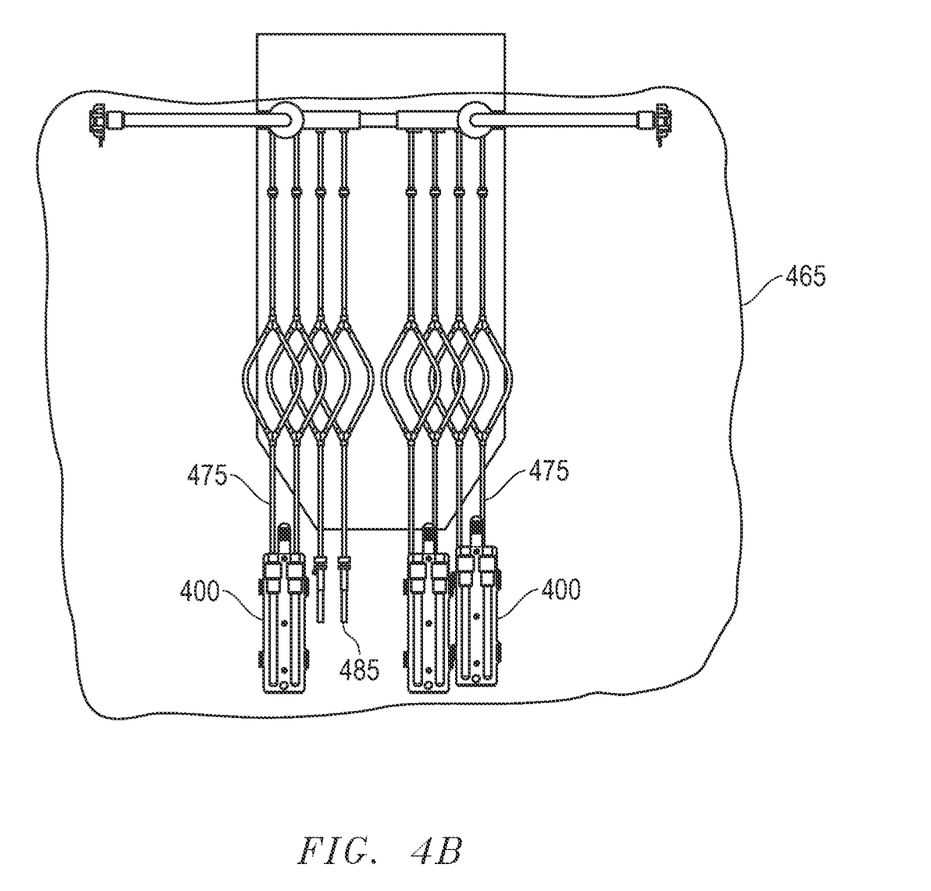
FIG. 4B illustrates a side view of a plurality of packaging containers attached to a plurality of tubes according to a number of embodiments of the present disclosure.

For purposes of illustration, FIG. 4A illustrates a side view of a packaging container attached to a tube according to a number of embodiments of the present disclosure. FIG. 4B illustrates a side view of a plurality of packaging containers attached to a plurality of tubes according to a number of embodiments of the present disclosure. In a number of embodiments, the packaging container may house multiple needle assemblies for use within a flexible vessel. A flexible vessel may be defined as any vessel capable of being punctured by needles, needle assemblies and other sharps. The flexible vessel may in some embodiments, be an isolator bag for use with an isolator. The flexible vessel may be made of a polymeric composition using any of the polymers listed above. In a number of embodiments, the flexible vessel may be a low density polyethylene film. The packaging container may prevent the needle assemblies from puncturing the flexible vessels. FIG. 4A shows a packaging container 400 attached to a tubing 475 as described above. The tubing 475 feeds through the void port 450. FIG. 4B shows a plurality of packaging containers 400, 400' attached to a plurality of tubings 475, 475' within a flexible vessel 465. FIG. 4B also shows a product in the form of a needle assembly outside of the packaging containers 400, 400.' Since the needle assembly is isolated from the flexible vessel 465 by the packaging container 400, 400', it will protect needles, needle assemblies and other sharps in the form of products while allowing improved ease of use.

A method for forming a packaging container may be described. The method may include providing a product. The method may further include providing a packaging container, including a body including a first portion including a coupling feature; a second portion including a coupling feature and complementary to the first portion; and a hinge portion coupling the first portion to the second portion. The method may further include moving the packaging container from an open position to a closed position around a product, where the first portion and the second portion combine to form a void port in the closed position around the product.

Use of the packaging container may provide increased benefits in several applications in fields such as, but not limited to, industrial, medical, health care, biopharmaceutical, pharmaceutical, drinking water, food & beverage, laboratory, dairy, or other types of applications. Notably, the use of the packaging container may protect the products from damage during shipping while allowing ease of use. Further, use of the packaging container for housing a product meant for sterilization, such as a medical device, pharmaceutical product, or biological product used in a surgical procedure may better maintain sterility of the product with an ease of transition from a closed position to an open position to remove the product without the use of any tools through the void port. This may provide optimal sealing engagement while allowing improved ease of use in difficult environments, such as operating rooms, bio-pharmaceutical or medical device production facilities, hospitals, or pharmacies.

Many different aspects and embodiments are possible. Some of those aspects and embodiments are described below. After reading this specification, skilled artisans will appreciate that those aspects and embodiments are only illustrative and do not limit the scope of the present invention.

Embodiment 1: A packaging container, comprising: a body comprising; a first portion comprising a coupling feature; a second portion comprising a coupling feature and complementary to the first portion; and a hinge portion coupling the first portion to the second portion adapted to move the packaging container from an open position to a closed position around a product, wherein the first portion and the second portion combine to form a void port in the closed position.

Embodiment 2: A packaging assembly comprising: a product; and a packaging container enclosing the product to provide a sterilize-able packaging assembly, wherein the packing bag comprising: a body comprising: a first portion comprising a coupling feature; a second portion comprising a coupling feature and complementary to the first portion; and a hinge portion coupling the first portion to the second portion adapted to move the packaging container from an open position to a closed position around a product, wherein the first portion and the second portion combine to form a void port in the closed position.

Embodiment 3: A method for forming a packaging container, comprising: providing a product; providing a packaging container, comprising: a body comprising: a first portion comprising a coupling feature; a second portion comprising a coupling feature and complementary to the first portion; and a hinge portion coupling the first portion to the second portion; and moving the packaging container from an open position to a closed position around a product, wherein the first portion and the second portion combine to form a void port in the closed position around the product.

Embodiment 4: The packaging container, packaging assembly, or method of any of the preceding embodiments, wherein in a closed position, the coupling feature of the first portion couples to the coupling feature of the second portion to form a packaging void for housing the product.

Embodiment 5: The packaging container, packaging assembly, or method of any of the preceding embodiments, at least one of the coupling feature of the first portion or the coupling feature of the second portion comprise multiple coupling features.

Embodiment 6: The packaging container, packaging assembly, or method of any of the preceding embodiments, wherein at least one of the coupling feature of the first portion or the coupling feature of the second portion comprises a fastener comprises at least one of screw threads or threadings, screws, bolts, clamps, clasps, clips, latches, pins, rivets, ties, nails, battens, buckle, flange, frog, grommet, hook-and-eye, peg, screw anchor, snap fastener, stitch, threaded fastener, tie, toggle bolt, wedge anchor, pin, groove and stop, nut and bolt, nut and screw, latch, handle, locking nut, tie rivet, male and female attachments, interlock attachments, or tongue- and groove attachments.

Embodiment 7: The packaging container, packaging assembly, or method of any of the preceding embodiments, wherein the packaging container comprises at least one of silicone, polydimethylsiloxane (PDMS), functionally modified polydimethylsiloxane, an polytetrafluoroethylene (PTFE), fluorinated ethylene-propylene (FEP), polyvinylidenfluoride (PVDF), polychlorotrifluoroethylene (PCTFE), ethylene chlorotrifluoroethylene (ECTFE), perfluoroalkoxypolymer (PFA), polyacetal (POM), polybutylene terephthalate (PBT), polyimide (PI), polyamidimide (PAI), polyetherimide, polyetheretherketone (PEEK), polyethylene, such as ultrahigh molecular weight polyethylene (UHMWPE), polysulfone, polyamide, polyphenylene oxide, polyphenylene sulfide (PPS), polyurethane, polyester, ethylene-tetrafluoroethylene (ETFE), tetrafluoro-ethylene-perfluoro (methyl vinyl ether) (MFA), polyvinylidene fluoride (PVDF), ethylene-chlorotrifluoroethylene (ECTFE), polyimide (PI), polyamidimide (PAI), polyphenylene sulfide (PPS), polyethersulofone (PES), polyphenylene sulfone (PPSO2), liquid crystal polymers (LCP), polyetherketone (PEK), polyether ether ketones (PEEK), aromatic polyesters (Ekonol), polyetherketone (PEK), liquid crystal polymer (LCP), polyamide (PA), polyethylene (PE), polypropylene (PP), polystyrene, styrene butadiene copolymers, polyesters, polycarbonate, polyacrylonitriles, polyamides, styrenic block copolymers, ethylene vinyl alcohol copolymers, ethylene vinyl acetate copolymers, polyesters grafted with maleic anhydride, poly-vinylidene chloride, aliphatic polyketone, liquid crystalline polymers, ethylene methyl acrylate copolymer, ethylene-norbomene copolymers, polymethylpentene and ethylene acrylic acid copoloymer, mixtures, copolymers, or any combination thereof.

Embodiment 8: The packaging container, packaging assembly, or method of any of the preceding embodiments, wherein the product is a needle or syringe.

Embodiment 9: The packaging container, packaging assembly, or method of any of the preceding embodiments, wherein the void port is adapted to at least partially house a part of a needle, syringe, or tubing in the closed position.

Embodiment 10: The packaging container, packaging assembly, or method of any of the preceding embodiments, wherein the body has a Shore A hardness in the range from 5 to 95, in a range from 15 to 80, in a range from 25 to 70, or in a range from 40 to 60.

Embodiment 11: The packaging container, packaging assembly, or method of any of the preceding embodiments, wherein the body has a Shore B hardness in the range from 5 to 95, in a range from 15 to 80, in a range from 25 to 70, or in a range from 40 to 60.

Embodiment 12: The packaging container, packaging assembly, or method of embodiment 4, wherein the packaging container comprises a plurality of voids in a closed position adapted to house a plurality of products.

Embodiment 13: The packaging container, packaging assembly, or method of embodiment 12, wherein the plurality of voids are separable from each other.

Embodiment 14: The packaging container, packaging assembly, or method of any of the preceding embodiments, wherein the packaging container is capable of forming a rollable or foldable position.

Embodiment 15: The packaging container, packaging assembly, or method of embodiment 14, wherein the packaging container comprises a locking mechanism adapted to lock the plurality of voids together in a rollable or foldable position.

Embodiment 16: The packaging container, packaging assembly, or method of any of the preceding embodiments, wherein the packaging container is capable of forming a stackable position.

Embodiment 17: The packaging container, packaging assembly, or method of any of the preceding embodiments, wherein the hinge portion is located at a first end of the packaging container.

Embodiment 18: The packaging container, packaging assembly, or method of any of the preceding embodiments, wherein the packaging container comprises a second end comprising a peelable or snappable tab adapted to at least partially seal the first portion and the second portion in the closed position.

Embodiment 19: The packaging container, packaging assembly, or method of embodiment 16, wherein the peelable or snappable film has an elastic modulus that is at least 0.5 times, at least 0.55 times, or at least 0.6 times the elastic modulus of the body of the packaging assembly, as defined in ASTM D 412.

Embodiment 20: The packaging container, packaging assembly, or method of any of the preceding embodiments, wherein the packaging container is adapted to be housed in a flexible vessel.

Embodiment 21: The method of any of embodiments 3-19, wherein the packaging container is formed by injection molding, vacuum forming, extrusion, additive manufacturing, or 3D-printing.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

Note that not all of the activities described above in the general description or the examples are required, that a portion of a specific activity may not be required, and that one or more further activities may be performed in addition to those described. Still further, the order in which activities are listed are not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed:

1. A packaging container, comprising:
    a body comprising;
        a first portion comprising a coupling feature comprising a fastener;
        a second portion comprising a coupling feature comprising a fastener and complementary to the first portion; and
        a hinge portion coupling the first portion to the second portion adapted to move the packaging container from an open position to a closed position around a product, wherein the first portion and the second portion combine to form a plurality of void ports in the closed position, each void port comprising a packaging void capable of housing the product, wherein the plurality of void ports are each disposed at the same end of the packaging container, wherein at least one of the coupling feature of the first portion and the coupling feature of the second portion comprises a punch allowing for pressing the first portion and the second portion together while maintaining the packaging void, wherein the packaging container further comprises a peelable or snappable tab adapted to at least partially seal the first portion and the second portion in the closed position, and wherein the tab may move the packaging container into an open position upon application of force by peeling or unsnapping the peelable or snappable tab.

2. The packaging container of claim 1, wherein in a closed position, the coupling feature of the first portion couples to the coupling feature of the second portion to form the plurality of packaging voids for housing the product.

3. The packaging container of claim 1, at least one of the coupling feature of the first portion the coupling feature of the second portion comprises multiple coupling features, wherein each coupling feature comprises a fastener.

4. The packaging container of claim 1, wherein at least one of the coupling feature of the first portion and the coupling feature of the second portion comprises at least one of screw threads, screws, bolts, clamps, clasps, clips, latches, pins, rivets, ties, nails, battens, buckle, flange, frog, grommet, hook-and-eye, peg, screw anchor, snap fastener, stitch, threaded fastener, tie, toggle bolt, wedge anchor, pin, groove-and-stop, nut-and-bolt, nut-and-screw, latch, handle, locking nut, tie rivet, male-and-female attachments, interlock attachments, and tongue-and groove attachments.

5. The packaging container of claim 1, wherein the packaging container comprises at least one of silicone, polydimethylsiloxane (PDMS), functionally modified polydimethylsiloxane, an polytetrafluoroethylene (PTFE), fluorinated ethylene-propylene (FEP), polyvinylidenfluoride (PVDF), polychlorotrifluoroethylene (PCTFE), ethylene chlorotrifluoroethylene (ECTFE), perfluoroalkoxypolymer (PFA), polyacetal (POM), polybutylene terephthalate (PBT), polyimide (PI), polyamidimide (PAI), polyetherimide, polyetheretherketone (PEEK), polyethylene, ultrahigh molecular weight polyethylene (UHMWPE), polysulfone, polyamide, polyphenylene oxide, polyphenylene sulfide (PPS), polyurethane, polyester, ethylene-tetrafluoroethylene (ETFE), tetrafluoro-ethylene-perfluoro (methyl vinyl ether) (MFA), polyvinylidene fluoride (PVDF), ethylene-chlorotrifluoroethylene (ECTFE), polyimide (PI), polyamidimide (PAI), polyphenylene sulfide (PPS), polyethersulofone (PES), polyphenylene sulfone (PPSO2), liquid crystal polymers (LCP), polyetherketone (PEK), polyether ether ketones (PEEK), aromatic polyesters (Ekonol), polyetherketone (PEK), liquid crystal polymer (LCP), polyamide (PA), polyethylene (PE), polypropylene (PP), polystyrene, styrene butadiene copolymers, polyesters, polycarbonate, polyacrylonitriles, polyamides, styrenic block copolymers, ethylene vinyl alcohol copolymers, ethylene vinyl acetate copolymers, polyesters grafted with maleic anhydride, poly-vinylidene chloride, aliphatic polyketone, liquid crystalline polymers, ethylene methyl acrylate copolymer, ethylene-norbornene copolymers, polymethylpentene and ethylene acyrilic acid copoloymer, mixtures, copolymers, and any combination thereof.

6. The packaging container of claim 1, wherein the product is a needle or syringe.

7. The packaging container of claim 1, wherein at least one void port of the plurality of void ports is adapted to at least partially house a part of one of a needle, syringe, and tubing in the closed position.

8. The packaging container of claim 1, wherein the body has a Shore A hardness in the range from 5 to 95.

9. The packaging container of claim 1, wherein the body has a Shore B hardness in the range from 5 to 95.

10. The packaging container of claim 1, wherein the fastener of the first portion comprises a snap fastener.

11. The packaging container of claim 1, wherein the peelable or snappable tab is located directly adjacent to the punch and offset from the plurality of void ports.

12. The packaging container of claim 1, wherein the packaging container is capable of forming a rollable or foldable position.

13. The packaging container of claim 12, wherein the packaging container comprises a locking mechanism adapted to lock the plurality of void ports together in a rollable or foldable position.

14. The packaging container of claim 1, wherein the packaging container is capable of forming a stackable position.

15. The packaging container of claim 1, wherein the hinge portion is located at a first end of the packaging container.

16. The packaging container of claim 15, wherein the packaging container comprises a second end comprising the plurality of void ports.

17. The packaging container of claim 1, wherein the peelable tab has an elastic modulus that is at least 0.5 times the elastic modulus of the body of the packaging assembly, as defined in ASTM D 412.

18. The packaging container of claim 1, wherein the packaging container is adapted to be housed in a flexible vessel.

19. A packaging assembly comprising:
a product; and
a packaging container enclosing the product to provide a sterilize-able packaging assembly, wherein the packing bag comprising:
a body comprising:
a first portion comprising a coupling feature comprising a fastener;
a second portion comprising a coupling feature comprising a fastener and complementary to the first portion; and
a hinge portion coupling the first portion to the second portion adapted to move the packaging container from an open position to a closed position around a product, wherein the first portion and the second portion combine to form a plurality of void ports in the closed position, each void port comprising a packaging void capable of housing the product, wherein the plurality of void ports are each disposed at the same end of the packaging container, wherein at least one of the coupling feature of the first portion and the coupling feature of the second portion comprises a punch allowing for pressing the first portion and the second portion together while maintaining the packaging void, wherein the packaging container further comprises a peelable or snappable tab adapted to at least partially seal the first portion and the second portion in the closed position, and wherein the tab may move the packaging container into an open position upon application of by peeling or unsnapping the peelable or snappable tab.

20. A method for forming a packaging container, comprising:
providing a product;
providing a packaging container, comprising:
a body comprising:
a first portion comprising a coupling feature comprising a fastener;
a second portion comprising a coupling feature comprising a fastener and complementary to the first portion; and
a hinge portion coupling the first portion to the second portion; and
moving the packaging container from an open position to a closed position around the product, wherein the first portion and the second portion combine to form a plurality of void ports in the closed position around the product, each void port comprising a packaging void capable of housing the product, wherein the plurality of void ports are each disposed at the same end of the packaging container, wherein at least one of the coupling feature of the first portion and the coupling feature of the second portion comprises a punch allowing for pressing the first portion and the second portion together while maintaining the packaging void, wherein the packaging container further comprises a peelable or snappable tab adapted to at least partially seal the first portion and the second portion in the closed position, and wherein the tab may move the packaging container into an open position upon application of force by peeling or unsnapping the peelable or snappable tab by peeling or unsnapping the peelable or snappable tab.

* * * * *